United States Patent [19]

Fortini et al.

[11] 4,024,247
[45] May 17, 1977

[54] COMPOSITION AND METHOD OF USING A PROTEIN MIXTURE DERIVED FROM LIVER

[75] Inventors: Jack G. Fortini, Oakland; Walter A. Blair, Palo Alto; Gerold M. Grodsky, San Francisco, all of Calif.

[73] Assignee: Palolab Pharmaceuticals Corporation, Menlo Park, Calif.

[22] Filed: Apr. 7, 1975
(Under Rule 47)

[21] Appl. No.: 565,864

Related U.S. Application Data

[60] Continuation-in-part of Ser. No. 212,741, Dec. 27, 1971, Pat. No. 3,876,774, which is a division of Ser. No. 212,341, Dec. 27, 1971, Pat. No. 3,701,768, which is a continuation-in-part of Ser. No. 763,292, Sept. 27, 1968, abandoned, which is a continuation-in-part of Ser. No. 307,404, Sept. 9, 1963, abandoned, which is a continuation-in-part of Ser. No. 5,376, Jan. 29, 1960, abandoned.

[52] U.S. Cl. .............................................. 424/177
[51] Int. Cl.² ................ A61K 17/02; A61K 27/00

[58] Field of Search ................................... 424/177

[56] References Cited
UNITED STATES PATENTS

| | | | |
|---|---|---|---|
| 3,701,768 | 10/1972 | Fortini et al. | 424/177 |
| 3,876,774 | 4/1975 | Fortini et al. | 424/177 |

*Primary Examiner*—Dolph H. Torrence
*Attorney, Agent, or Firm*—Limbach, Limbach & Sutton

[57] ABSTRACT

A composition of matter and method useful in treating certain disease conditions by virtue of a protein mixture having a variety of disparate properties, such as facilitating wound healing and influencing glucose metabolism. It also exhibits pronounced superoxide dismutase activity. The composition may supplant or be combined with cortico-steroids to provide anti-inflammatory response while facilitating wound healing. It increases the rate of urea nitrogen synthesis, reduces peripheral blood ammonia, simultaneously facilitates glucose uptake and glycogen deposition. It is useful for treating hepatitis, arthritis, and scar tissue.

7 Claims, 1 Drawing Figure

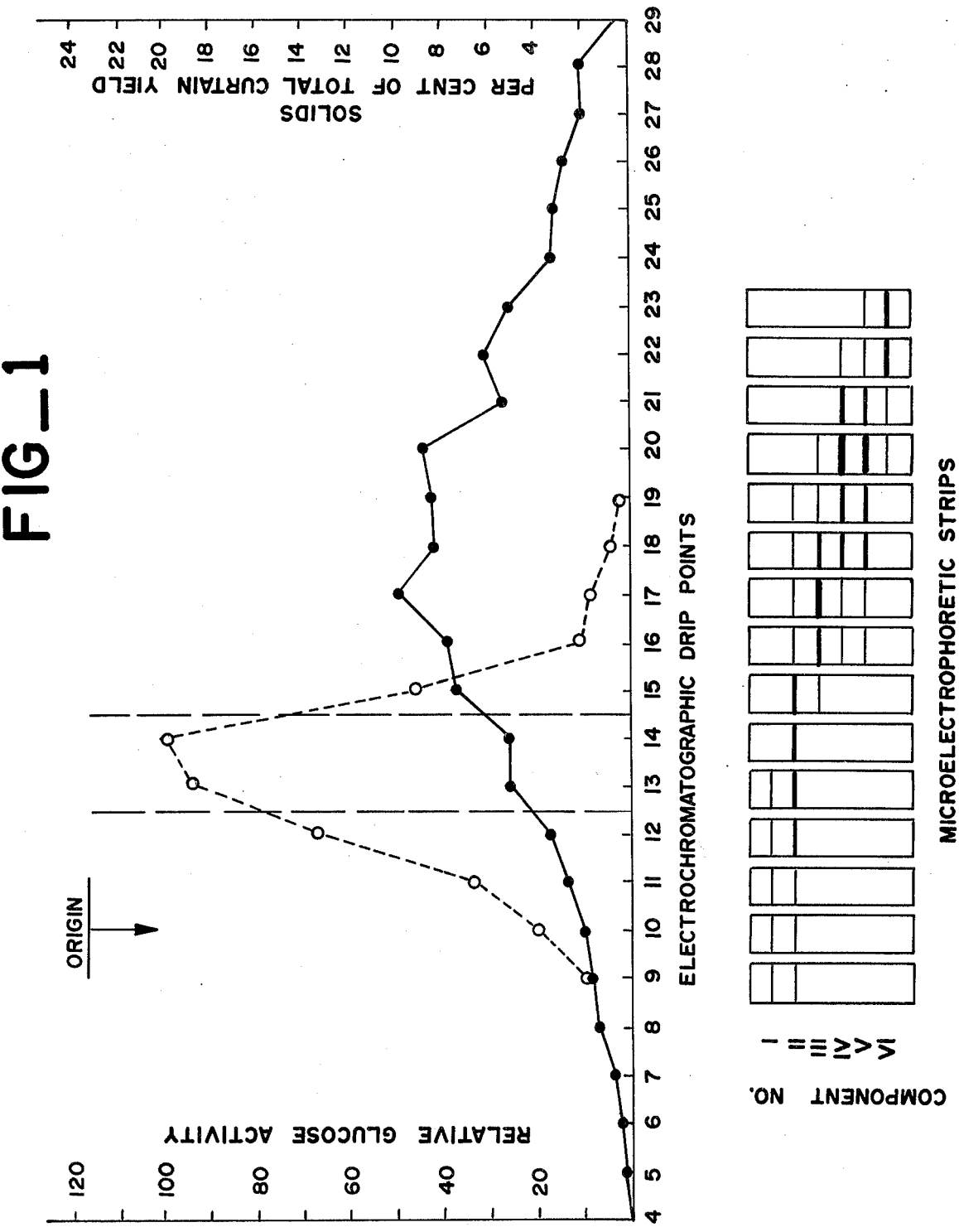

COMPOSITION AND METHOD OF USING A PROTEIN MIXTURE DERIVED FROM LIVER

CROSS REFERENCES

This application is a continuation-in-part of application Ser. No. 212,741, filed Dec. 27, 1971, now Pat. No. 3,876,774, which is a division of application Ser. No. 212,341, filed Dec. 27, 1971, now U.S. Pat. No. 3,701,768, which is a continuation-in-part of application Ser. No. 763,292, filed Sept. 27, 1968, now abandoned, which is a continuation-in-part of application Ser. No. 307,404, filed Sept. 9, 1963, now abandoned, which is a continuation-in-part of application Ser. No. 5,376, filed Jan. 29, 1960, now abandoned.

BACKGROUND OF THE INVENTION

This invention relates generally to a method of using and a composition of a physiologically active protein mixture which exhibits a variety of disparate properties, such as facilitating wound healing and influencing glucose metabolism. More particularly, the invention relates to a composition which is derivable from liver and has the ability to increase glucose uptake and glycogen synthesis. It also exhibits pronounced superoxide dismutase activity.

The preparation of extracts from liver has gained the attention of many workers, largely because of the great number of biologically active materials present in liver. The extraction process of the present invention is similar in its initial steps to the process described in the article by Mohamed and Greenberg (Archives of Biochemistry, 8:349, 1945) for the derivation of the enzyme arginase but the present method makes use of a supernatant liquid which is discarded according to the procedure of Mohamed and Greenberg. Furthermore, the protein of the present invention exhibits physiological activity entirely different from liver arginase.

Very few agents exist which facilitate the absorption of energy sources, such as glucose, into the cells. Most proteins inhibit glucose uptake. One of the few proteins which facilitates glucose uptake and glycogen synthesis is insulin. There is a need for additional proteins manifesting these two properties in combination.

Superoxide dismutases are a group of enzymes believed to catalytically scavenge the superoxide radical, which appears to be an important agent of the toxicity of oxygen. See Fridovich "Superoxide Dismutases," 1975 Annual Review of Biochemistry, p. 147.

SUMMARY OF THE INVENTION

In our U.S. Pat. No. 3,701,768, there is disclosed and claimed a method of extracting a protein mixture from liver and the resulting product. The present application relates to compositions of the product and to the method of using the product there disclosed.

The product of the present invention influences the primary metabolism of carbohydrate and the urea cycle. The product is a biological catalyst present in large amounts in liver. It increases glucose uptake and glycogen synthesis in incubating muscle, increases glucose metabolism in isolated perfused liver and increases glycogen storage in adrenalectomized animals. It acts in vivo to improve renal functions in intact animals, indicating that it is humorally transported and enters peripheral cells or influences their metabolism at the membrane level. The product exhibits pronounced superoxide dismutase activity. It is useful in reducing peripheral blood ammonia; in treating scar tissue, arthritis and hepatitis; and in facilitating tissue repair at the same time as it inhibits inflammation.

The wound healing effect of this invention is of particular interest because the product also inhibits inflammation. This combination of properties is unusual. The most widely used anti-inflammatory agents, the cortico-steroids, inhibit wound healing, thus limiting the usefulness of these agents. Tissue damage and inflammation frequently occur together, and the use of conventional agents like hydrocortisone actually prolongs the healing duration. There is, therefore, a need for an anti-inflammatory agent which also facilitates wound healing.

By combining the product of this invention with hydrocortisone, smaller doses of the sometimes toxic cortico-steroids may be used with greater anti-inflammatory response than with full doses of cortico-steroids alone.

BRIEF DESCRIPTION OF THE DRAWING

FIG. 1 is an electrochromatogram showing a typical electrophoretic pattern of the crude product containing six protein components.

DESCRIPTION OF THE PREFERRED EMBODIMENT

The biologically active ingredients of the present invention are conveniently extracted from liver. The process, described in our prior U.S. Pat. No. 3,701,768, may be briefly summarized by the following steps:

(1) treating liver with an aqueous solution of divalent metal activating cation at a pH essentially neutral or slightly alkaline and separating the resultant solids from the liquid;

(2) treating the liquid with heavy metal precipitating agent and separating the resultant precipitate from the liquid;

(3) adjusting the pH of the liquid from step (2) to a range of between 8.3 and 8.5 and separating the resultant precipitate from the liquid;

(4) treating the liquid from step (3) with a concentrated solution of salting out agent to precipitate undesired protein and separating the protein precipitate from the liquid;

(5) adding solvent to the liquid from step (4) in an amount sufficient to give the resultant mixture a solvent concentration of 20 to 26% by volume and separating the resultant precipitate from the liquid; adding solvent to the liquid in an amount sufficient to give the resultant mixture a solvent concentration to 35 to 40% by volume to produce a mixture having three layers; separating the upper layer and adding to it in amount sufficient to give the resultant mixture a solvent content 70 and 77% by volume whereby protein is precipitated;

(6) separating the protein precipitate and dispersing it in a solvent as a pH of 7.8 to 8.2;

(7) dialyzing the dispersion from step (6);

(8) heating the dialyzate from step (7) to a temperature between 46 and 50° C. and separating the resultant precipitate from the liquid;

(9) subjecting the liquid from step (8) to electrophoresis and recovering a biologically active mixture.

The product described in our prior patent is designated as to source by the registered trademark Acutalyn. For simplicity in this application, the term Acutalyn crude shall mean the crude product derived from Step 8 of FIG. 1 of the prior patent, having the six discrete components shown in FIG. 2 of the patent. The designations Acutalyn crude and crude product will be used herein interchangeably to designate the material which contains all of the components of the product of step 8.

The term "dialyzate" in step 8 of the above described process refers to the material which fails to pass through the dialysis membrane.

As described in our prior patent, one of the components is designated Component II. This material makes up about 15–20% of the Acutalyn crude. For consistency in this application, this component will be referred to as Fraction A. It appears that Fraction A is associated with the protein component which gives Acutalyn crude its pronounced superoxide dismutase activity. The percent of superoxide dismutase activity varies from about 7 to 35% of the Acutalyn crude, as determined by direct enzymatic assay.

Also included in Acutalyn crude is a biologically active protein of approximately 25,000 molecular weight which is described in our prior patent.

FIG. 1 is a graphical representation of the relative glucose activity of the various drip points of an electrophoretic curtain. The crude product solution derived from the process described in our Patent 3,701,868 is placed on the curtain at the point indicated "origin" in FIG. 1. Also shown in FIG. 1 are the amounts of solids obtained at the different drip points, indicated as percent solids of total curtain yield. Relative activity for stimulating glucose metabolism is shown in a broken line curve and the solid line curve is indicated as solids present.

It will be noted that the broken line curve peaks sharply at drip points 13 and 14, showing that the glucose activity is greatest in this fraction. The fraction obtained from drip points 13 and 14 is designated "Component II".

Beneath the graph of FIG. 1 in registry with the drip points on the abscissa are representations of microelectrophoretic strips used to indicate the protein components at each drip point. Samples of the product from each of drip points 9 through 23 were taken. Each of these samples was adjusted to a concentration of about 5,000 mcg per ml. Cellulose acetate strips 25 mm. in width were provided and a small quantity of drip point sample was applied at the center of each strip. Each strip so tested was subjected to electrophoresis in a microelectrophoresis unit described by Grunbaum and Kirk in Analytical Chemistry, Vol. 32, page 563 (1960). A direct current voltage of 150 volts was applied for 90 minutes. Each strip was then dried and immersed in a 0.2% solution of Ponceau-S stain in 3% aqueous trichloracetic acid for 5 minutes and then rinsed with 5% acetic acid solution and with water and dried at room temperature between blotters.

The horizontal black bands on each of the strips represent a particular protein (or protein-like) component or fraction of the material from the respective drip point, and the width of the band indicates schematically the relative amount of such material. To the left of the strips in FIG. 1, the Roman numerals I through VI appear in registry with six such marks or bands. It will be seen that band II is predominant in the material from drip points 13 and 14. This component is present in lesser quantities in the strips from drip points 9 to 12 and 15 to 19. As will be seen, the stips 13 and 14 corresponding to the drip points 13 and 14 have the highest proportion of Component II, also by far the highest relative glucose ability to stimulate metabolism.

One important activity of Acutalyn crude is its ability to increase glucose uptake by incubating muscle diaphragm of the rat in vitro. The comparative reproducibility of the effect in an in vitro system provides a useful system for both establishing a basic action of the substance and for providing a technique for bioassay. The rat diaphragm system employed was based on earlier methods by Gemmill (Bull. John Hopkins Hospital, Vol. 68, page 329, 1941) and Willebrands, et al. (Science 112, page 277, 1950).

EXAMPLE 1

The predetermination of glucose activity of Acutalyn crude, (as well as Fraction A and the protein of U.S. Pat. No. 3,701,768) was made by preparing an aqueous solution of 280 grams of sodium chloride, 14.8 grams potassium chloride and 12.0 grams $MgSO_4 \cdot 7H_2O$ per liter (referred to as Stock Solution I) and an aqueous solution of 90.8 grams $NaHCO_3$, 6.0 grams $Na_2HOP_4 \cdot 7H_2O$, 1.2 grams $KH_2PO_4$ and 180 mg. phenol red per liter (referred to as Stock Solution II) were prepared. 25 ml. of Stock Solution I and 25 ml. of Stock Solution II were diluted with 900 ml. of water, and 2 ml. of 25% (by weight per volume) of $CaCl_2 \cdot 6H_2O$ solution were added and the solution was gassed with 95% oxygen-5% $CO_2$ and was made up to 1 liter.

This is referred to as Basic Salt Solution. A Glucose Basic Salt Solution was prepared by dissolving 3.0 grams of reagent grade anhydrous D-glucose in one liter of Basic Salt Solution.

A quantity of material from each drip point of FIG. 1 was diluted with Glucose Basic Salt Solution so that it contained $5.0 \times 10^{-5}$ mcg (microgram) of protein solids per ml. of solution. This will be referred to as Test Solution. Male Sprague Dawley rats (a standard laboratory strain of rats) each weighing 100± 10 grams were selected and maintained under identical dietetic and environmental conditions for at least five days before the tests described hereinafter. For 24 hours immediately preceding the test each animal was fasted on a wire screen in a separate cage with free access to water. Each animal was killed by decapitation and its hemidiaphragms were removed by means of a punch designed for this purpose specifically to insure uniformity in cut and weight of tissue samples. Each pair of hemidiaphragms from an animal was washed, placed on hardened filter paper, blotted slightly, then placed in a flask containing Gey and Gey buffer (Amer. J. of Cancer 27:54, 1936). Reagent grade D-glucose (anhydrous) was included to a final concentration of 300 mg/100 ml. Samples of the invention at varying concentrations ($2 - 10 \times 10^{-4}$ mg.) were added to 2 ml. of buffer which was incubated with the tissue and with shaking under an atmosphere of 95% oxygen 5% $CO_2$. Typical incubation periods were 90 minutes. Hemi-diaphragms were removed, dried, and weighed.

Glucose content was determined in the flask before and after incubation by method of Somogyi, Bio. Chem. 160:62, 1945. Glucose uptake was calculated as milligrams of glucose per 100 milliliters of buffer per 100 milligrams of dried tissue. Glucose uptake is facilitated with increased concentration of the protein of the invention in a log-dose relationship. The glucose uptake activity on a weight to weight basis is superior with the present composition than with insulin.

Acutalyn crude resembles insulin in a number of significant ways. Particularly, insulin increases the uptake of glucose in muscle, such as rat diaphragm. The Acutalyn crude has substantially greater activity than insulin in this respect as noted in Example 1. However, it differs from insulin in that it has no influence on blood glucose levels in the intact animal. Further, Acutalyn crude prolongs the survival of isolated perfused rabbit liver as measured by its metabolic activity in oxygen consumption and carbon dioxide production. Insulin fails to produce either of these effects.

The influence on tissue glucose uptake and increased synthesis of liver glycogen without resulting hypoglycemia constitutes a mobilization of energy for overcoming certain disease states. Acutalyn crude is useful in counteracting stress — caused shock and damage, including experimentally induced uremia, reticuloendothelial damage and decreased survival from administered 6-mercaptopurine and AET.

Acutalyn crude also is useful in facilitating tissue repair. The next two examples relate to the property of enhancing recovery of soft tissue lesions. In horses, fistulous tracts are a chronic condition because they are characteristically lined with a false or adventitious membrane and are exceedingly difficult to heal.

EXAMPLE 2

Ten horses with suppurative lesions consisting of fistulous withers, quittor, fistula of the hock, and traumatic podermatitis were selected for treatment. Where necessary, surgical drainage was established and the usual standard management techniques were applied. Acutalyn crude, equine potency (125 mg. pct.), was injected intravenously in 5 ml. doses every two to every four days. Total number of injections were two to ten per animal. Dosage for each individual case is given in Table I.

TABLE I

| Case No. | Condition | ml. per Inj. | Freq. Days | No. of Inj. | Response |
|---|---|---|---|---|---|
| 5 | Fistulous withers | 15 | 1 | 7 | Accelerated healing. |
| 13 | Fistulous withers | 5 | 4 | 4 | Healed without usual complications. |
| 19 | Fistulous withers | 5 | 3 | 2 | No surgery. Aspirated; healed. |
| 21 | Fistulous withers | 5 | 2 | 4 | Slow response. Relapse nine months. |
| 22 | Fistulous withers | 5 | 2 | 4 | Healed with no relapse. |
| 23 | Fistulous withers | 5 | 2 | 4 | Healed with no relapse. |
| 78 | Quittor | 5 | 1 | 2 | No response. |
| 82 | Quittor | 5 | 1 | 2 | Progressive improvement. |
| 14 | Fistula hock | 5 | 2 | 4 | Remarkable recovery. |
| 97 | Traumatic pododermatitis | 5 | 2 | 10 | Surgical wound healed rapidly. |

Of the ten clinical cases studied, eight had excellent responses to therapy. These reponses were judged using two criteria. The first was the progressive healing of a chronic lesion which had defied all prior attempts to manage the condition. The second was the incidence of relapse during a two year followup period.

Case No. 19, a fistulous withers, was treated early in the course of the condition. No surgical drainage was employed; the lesion was simply aspirated and intravenous product of Example 1 was administered. Healing was complete, and in this case as in the other cases there was no relapse.

The horses under study all had conditions which are well known for their tendency to recur. A relapse occurred in only one horse, Case No. 21. This animal responded to therapy with a slow healing period and relapse nine months later. Case No. 78, the treatment of a quittor, was unsuccessful. There was no apparent response to therapy. The results of this clinical part of the study are summarized in Table II.

EXAMPLE 3

Ten horses which were candidates for slaughter were selected for experimentally induced soft tissue lesion. Each animal received 30 cc. of 25% chloral hydrate solution injected extraveneously to produce the desired acute lesion. Four horses, Nos. 1, 3, 9, and 10, received this injection intramuscularly in the neck region; the remaining six animals were injected extraveneously in the area of the jugular vein at the usual site of intravenous injections.

Following the injection of chloral hydrate, Animal No. 1 received no immediate therapy; Animal No. 2 received chymotrypsin intramuscularly; Animals Nos. 3 through 10 all received Acutalyn crude intravenously. No additional Acutalyn crude was administered to the horses after the first day, except Animal No. 8 which received one intravenous injection daily for five days and Animal No. 1 which received one intravenous injection on the seventh day with the hope of stopping or preventing the necrosis and slough of tissue.

Animals Nos. 4, 5, 6, and 7 received Acutalyn crude, the usual equine potency. Animals Nos. 1, 3, 8, 9, and 10 received injections of 100 units each of Fraction A.

The control experience of incidence of development of the typical lesion caused by chloral hydrate injected into the tissues surrounding the jugular vein has been 100%. Case Nos. 1 and 2 developed this typical lesion by the sixth day. The lesion progressed to the necrotic stage and the animal was sacrificed.

The Acutalyn crude treated animals all demonstrated a significantly lesser degree of inflammation and swelling than the controls. In these treated horses, the slight to moderate lesion which developed by the sixth day regressed rapidly. Complete disappearance of the lesion was observed between the seventh and the twelfth day. Most important was that the lesion did not progress and therefore there was no necrotic or sloughing stage.

In Cases Nos. 9 and 10, which received Component A, there was an apparent complete protective effect. There was no evidence whatsoever of any tissue reaction. Case No. 1, which received one injection of the Acutalyn crude on the seventh day, after the lesion had developed to full size, responded promptly with the necrotic lesion resolving. By the twelfth day healing was complete. The results of this experimental part of the study are summarized in Table II.

TABLE II

| TREATMENT OF EXPERIMENTAL LESIONS | | | |
|---|---|---|---|
| First Day | Sixth Day | Seventh Day | Twelfth Day |
| No. 1 – 30 cc chloral | Swelling size of | Tmt: Acutalyn | Swelling and |

TABLE II-continued
TREATMENT OF EXPERIMENTAL LESIONS

| First Day | Sixth Day | Seventh Day | Twelfth Day |
|---|---|---|---|
| hydrate I.M. (neck) No treatment | football, sterile abscess sloughing | 5 ml. I.V. | abscess gone, lesion healed. |
| No. 2 – 30 cc chloral hydrate I.M. (neck) Tmt: Chymotrypsin I.M. | Swelling, abscess, sloughing. Similar to case No. 1. | Tmt: None, lesion progressing in intensity | Animal sacrificed with extensive local necrosis at injection site |
| No. 3 – 30 cc chloral hydrate I.M. (neck) Tmt: Acutalyn 10 ml. I.V. | Swelling about half size of lesion on case No. 1. No abscess, no sloughing | Tmt: None Swelling receding | Lesion healed |
| No. 4 – 30 cc chloral hydrate extravenous Tmt: Acutalyn 5 ml. I.V. | Moderate swelling, no abscess, no sloughing | Tmt: None Swelling receding | Lesion healed. |
| No. 5 – 30 cc chloral hydrate extravenous Tmt: Acutalyn 5 ml. I.V. | Moderate swelling. No abscess, no sloughing. | Tmt: None Swelling receding. | Lesion healed. |
| No. 6 – 30 cc chloral hydrate extravenous Tmt: Acutalyn 5 ml. I.V. | Moderate swelling, no abscess, no sloughing | Tmt: None. Swelling receding. | Lesion healed |
| No. 7 – 30 cc chloral hydrate extravenous Tmt: Acutalyn 5 ml. I.V. | Moderate swelling, no abscess, no sloughing | Tmt: None. Swelling receding. | Lesion healed. |
| No. 8 – 30 cc chloral hydrate extravenous Tmt: Acutalyn 10 ml. IV daily for 5 days | Severe swelling first 24 hours after chloral hydrate injection, then rapidly receded. | Tmt: None. Normal | Lesion healed. |
| No. 9 – 30 cc chloral hydrate I.M. (neck) Tmt: Acutalyn 10 ml. I.V. | No external evidence of local soft tissue reaction. | Tmt: None. Normal appearance. | Normal. |
| No. 10 – 30 cc chloral hydrate I.M. (neck) Tmt: Acutalyn 10 ml. I.V. | No external evidence of local soft tissue reaction. | Tmt: None. Normal appearance. | Normal. |

Seven of the eight animals injected with chloral hydrate into the muscle tissues and treated intravenously with Acutalyn crude developed a slight to moderate swelling without necrosis which suggests a beneficial protective effect. One horse, Case No. 8, showed severe swelling for the first 24 hours which receded rapidly to normal by the seventh day. Two of these horses exhibited complete protection; there was no evidence of any swelling or any local tissue reaction. By the sixth day a typical lesion developed in the two untreated cases and progressed into the cecrotic stage. Delayed treatment of Case No. 1 with Fraction A produced a rapid response at that stage and the lesion was completely healed by the twelfth day.

Examples 2 and 3 illustrate the anti-inflammatory properties of Acutalyn which has been described and claimed in our U.S. Pat. No. 3,876,774, issued Apr. 8, 1975. In addition, however, these examples illustrate the wound healing effect of the composition.

EXAMPLE 4

A more precise measure of the wound healing effect of Acutalyn crude is demonstrated by determining the tensile strength of healing wounds. In this example, a determination was made of the force required to rupture a surgically induced wound which has been healed with or without Acutalyn crude. A solution of Acutalyn crude was prepared of 18 mg. solids per ml. 0.25 ml. of this solution was injected into guinea pigs each day for 10 days. On the eleventh day, a 1½ inch wound was cut on either side and parallel to the spinal column of a 500–700 gram female guinea pig. The wound was then sutured according to standard surgical procedures and a test substance was administered subcutaneously once daily for 10 days. On the 11the day the wounded skin was removed en bloc and quick frozen and stored at −92° C. Later the same day the tissue specimens were removed from storage, immediately immersed in a water bath at 24° C. so as to bring the tissue to ambient temperature, and finally cut into strips 1.6 mm. wide with a special cutter. The stips were cut perpendicular to the wound so that the incision was positioned in the center of the strip.

One end of the strip was attached 1 cm. away from the incision to a Grass FT 0.03 Force Transducer and the other end was attached (also 1 cm. from the incision) to a mechanical device which pulled the specimen at the rate of 0.7 mm/sec. The force was recorded on a Grass Polygraph 7B.

The results are illustrated in the attached Table III. Significantly greater force was required to rupture wounds healed with the benefit of the composition of the present invention.

TABLE III.

| | Animal Number | | | | | | | | | |
|---|---|---|---|---|---|---|---|---|---|---|
| | 1 | 2 | 3 | 4 | 5 | 6 | 7 | 8 | 9 | 10 |
| Body Weight | | | | | | | | | | |

TABLE III.-continued

| | Animal Number | | | | | | | | | |
|---|---|---|---|---|---|---|---|---|---|---|
| | 1 | 2 | 3 | 4 | 5 | 6 | 7 | 8 | 9 | 10 |
| Initial | 342 | 410 | 345 | 300 | 426 | 462 | 414 | 354 | 286 | 407 |
| Final | 440 | 485 | 406 | 358 | 484 | 550 | 484 | 428 | 333 | 466 |
| Force applied (grams) at time of rupture | | | | | | | | | | |
| Test No. 1 | 113 | 113 | 75 | 113 | 125 | 263 | 175 | 250 | 213 | 150 |
| Test No. 2 | 150 | 188 | 100 | 113 | 138 | 163 | 163 | 250 | 263 | 125 |
| Test No. 3 | 125 | 138 | 113 | 113 | 113 | 213 | 200 | 200 | 163 | 125 |
| Test No. 4 | 113 | 163 | 113 | 125 | 163 | 175 | 213 | 163 | 163 | 100 |
| Test No. 5 | 138 | 125 | 100 | 113 | 200 | 250 | 239 | 213 | 163 | 125 |
| Test No. 6 | 113 | 138 | 113 | 113 | 113 | 213 | 263 | 150 | 188 | 125 |
| Test No. 7 | 225 | 213 | 88 | 100 | 138 | 213 | 150 | 200 | 275 | 150 |
| Test No. 8 | 125 | 138 | 113 | 113 | 188 | 163 | 138 | 250 | 275 | 150 |
| Test No. 9 | 225 | 88 | 138 | 138 | 125 | 125 | 125 | 250 | 150 | 113 |
| Test No. 10 | 163 | 138 | 163 | 150 | 100 | 200 | 288 | 213 | 175 | 175 |
| Average | 149 | 144 | 113 | 119 | 140 | 198 | 195 | 214 | 203 | 134 |
| Standard Deviation | 43.3 | 36.0 | 32.3 | 14.7 | 33.2 | 42.1 | 54.9 | 36.9 | 50.2 | 22.0 |

Animals 1-5 were controls treated only with sterile saline solution. Animals 5-10 were treated with the composition of Example 1 in a dosage of 0.25 ml/day.

Clinical studies also show the ability of the protein of the present invention to systemically enhance softening of chronis urethral strictures the humans and to cause these strictures to dilate easily without local anesthetic and to remain dilated for periods of one to five or more years without need for further therapy of any kind.

EXAMPLE 5

The product of this invention may be combined with cortisteroids to give a greater anti-inflammatory response than either drug along. In this test, Acutalyn crude was used alone and in combination with hydrocortisone to determine the inhibition of inflammation according to a standard test for carrageenan paw edema using the method described in Winter, E. Risley, E. A., and Nuss (G. W. PROC. SOC. EXPTL. BIOL. & MED.), 111:544 (1962). Briefly stated, the anti-inflammatory effect of a drug may be measured by injecting a known irritant into the paw of a rat and volumetrically measuring the degree of swelling of the paw. This standardized test gives a comparison between a control of saline solution and indicates the amount of reduction in swelling resulting from different dosage levels.

The effect using Acutalyn crude product was measured alone and the effect of hydrocortisone alone was also measured, first in its half dosage form and then full dosage. Then the inhibition of the two dosage forms in combination with crude product were determined. Table IV shows the results. The combined effect was significantly better than either drug alone. The sometimes undesirable side effects of hydrocortisone, such as inhibiting wound healing, can be minimized by reducing the dosage in half and combining Acutalyn crude, with the net result of significantly improved results over even full strength hydrocortisone. Hydrocortisone was given in standard dose of 1.2 ml per Kg of animal weight of 27.4 mg/ml in 0.5% gum arabic. Acutalyn crude was given in a dose of 1.2 ml/Kg of animal weight of 15.75 mg of dry solids per ml.

TABLE IV.

| | % Inhibition of Carrageenan induced edema |
|---|---|
| Acutalyn crude | 21% |
| Hydrocortisone - ½dose | 50% |
| Hydrocortisone - standard dose | 53% |
| Combined Hydrocortisone (standard dose) | |

TABLE IV.-continued

| | % Inhibition of Carrageenan induced edema |
|---|---|
| and Acutalyn | 63% |
| Combined Hydrocortisone (half dose) and Acutalyn | 65% |

EXAMPLE 6

This example relates to the utility of the invention in the treatment of scar tissue, specifically urethral strictures.

Prior to the introduction of Acutalyn therapy, 44 of the 51 patients in the study had chronic urethral strictures requiring routine treatment at regular intervals, some as often as four times monthly, for periods ranging from 1 year to 42 years. Twenty-four patients had been treated at regular intervals for over 10 years prior to Acutalyn therapy; another 14 cases had been treated at regular intervals for two or more years. Many had difficult filiform strictures; many also had required anesthetic for passage of sounds. The addition of Acutalyn was the only change in their routine therapy. The Acutalyn preparation used in this study contained all the components of Actualyn crude, ampulized into human dosage form containing 50 mg. %. All injections were administered either IV or IM.

Patients were kept under treatment until their prostatitis cleared and 30 French sounds could be passed without discomfort or difficulty and without previous local anesthesia. If the improved condition persisted after treatments were stopped for six months, and then for one year, all treatments were discontinued. The strictures were not considered "cured" until after the lapse of several years in which no therapy was required and there was no evidence of a stricture.

There were favorable responses in 45 cases. 23 cases remined free of urethral strictures without requiring additional Acutalyn or other therapy during a long period of follow-up ranging from one to four years. The stricture returned in eight cases after periods of several months to three years. Four cases had only partial or temporary improvement; they required additional Acutalyn therapy. Three cases could not be evaluated.

Acutalyn therapy varied from one injection to as many as 53 injections over a period of several years. There were no adverse effects.

EXAMPLE 7

Acutalyn crude has been used effectively in treating chronic and severe hypertrophic, pruritic and painful burn scars. In this example, an adult human male was suffering from deep dermal and third degree burns of his right upper arm and elbow. The patient had been unable to rest and sleep for months because of the severe itching on the burn scars. The patient was given Acutalyn crude (50 mg. %) twice weekly by injection either intravenously or intramuscularly for a total of 11 injections. The itching subsided and the patient was able to rest after the first injection. The remission was complete.

EXAMPLE 8

In this example a young man, age 23, was suffering with an unsightly and pruritic keloid of the left ear. It covered one-third of the posterior surface of the ear. It was recurrent, beginning 16 years earlier following otoplasty. It was resistant to all therapy. Within one to 3 months following surgical excision on five occasions the keloid returned to a more severe degree each time. Acutalyn crude injections were initiated at 3 day intervals. After the fourth injection, there was a relief in symptoms, including relief of pruritis, itching, and tenderness, and reduction in size of the keloid, which continued to improve as long as Acutalyn therapy was used. Following 10 additional injections at 3 day intervals, the keloids were excised. Seven Acutalyn injections were given at 3 day intervals following surgery and again one month later; no other therapy was given. Acutalyn injections were resumed five months later and continued at irregular intervals. The keloid did not return for ten months. When Acutalyn crude was discontinued, keloid growth returned, through not as large as previously. The itching and tenderness disappeared completely and keloid flattened out to normal skin condition. Three years later, the condition remained free of keloidal recurrence.

The following four examples relate to the treatment of arthritis and related disorders. In the great majority of patients there was a decrease in disability, pair, swelling, cessation of muscular spasm, disappearance of nodules, improvement in clinical chemistries, and a return of function in severe disabling cases, as well as in acute cases. Acutalyn therapy enabled patients on long-term corticosteroid, phenylbutazone, and gold therapy suffering severe side effects to be withdrawn gradually from the toxic therapy with continuing improvement of their arthritic symptoms. 50 mg. % Acutalyn crude was used.

EXAMPLE 9

This example illustrates how use of Acutalyn crude enables chronic arthritis patients suffering severe side effects from long-term corticosteroid therapy to be withdrawn from cortisone therapy without ill-effects, and with dramatic improvement in arthritic symptoms and disappearance of hypercortisonism symptoms. The patient in this example was a 53-year old female with a diagnosis of chronic rheumatoid arthritis, Stage III structural changes, Class III functional impairment, peripheral joint involvement, with chronic, advanced, exogenous hypercortisomism, Cushing's syndrome, seven years duration, resulting from long-term corticosteroid therapy. Patient was an opera singer who was unable to continue her operatic career or to practice singing because of these problems. Previous therapy included prednisolone plus salicylates.

Examination revealed typical fusiform swelling of fingers and inability to grasp objects; definite swelling of both elbows with limitation of extension; limitation of rotation, flexion, and lateral tilt of neck. Inability to elevate arms fully because of shoulder involvement; both knees swollen, with limitation of flexion. Examination also revealed very typical Cushing's syndrome, with moon face, buffalo hump, depression, considerable hirsutism, and other metabolic problems.

Injections of Acutalyn crude, 50 mg. %, i.v. were given twice weekly for 9 weeks and the patient was tapered off cortico-steroids gradually over an eight-day period. Following the third injection, patient noted more flexibility of all joints and ability to clench fists. Following seventh injection, Cushing's syndrome was gone and skin texture was soft and appeared much more youthful. Following ninth injection, the patient was able to ambulate, turn head easily, and had full extension of both arms as well as ability to raise arms above head. Her appetite was much improved. Six weeks after the first injection, the patient was able to resume singing practice. During the period of steroid withdrawal patient had superficial infections and was given antibiotics. Final examination at the end of ninth week revealed complete restoration of all joint mobility; rheumatic involvement completely disappeared; freedom from all pain; complete disappearance of classical Cushing's syndrome and chronic exogenous hypercortisonism; feeling of well-being, resumption of operatic career and normal household duties; full and complete reversal to normalcy. There were no toxic reactions or hematological abnormalities. During the course of treatment, patient lost 17½ lbs. Final laboratory findings: Hb. 13.8 gms.; erythrocytes 4,510,000 per cu. mm.; leukocytes 9,500 per cu.mm.; eosionophiles 2%; normal differential; corrected sedimentation rate 22 mm./hr.

EXAMPLE 10

The patient in this case was a female, age 39, with a diagnosis of Osteoarthritis, stage II structural changes, class II functional impairment, three years duration. Previous therapy included injections of hydrocortisone into shoulder and finger with no relief. Examination revealed both hands severely swollen, red, painful nodes, distal phalanges (Herbenden's nodes), painful right shoulder, weak grip right hand. A total of eight 5.0 ml. injections of Acutalyn crude, 50 mg. %, were given i.v., one weekly for four weeks, then bi-weekly for eight weeks. Symptoms began to improve following the first injection, with decrease in pain. Following the third injection, the nodes on fingers were softer, following the fourth injection there was marked improvement in both swelling and pain. The pain disappeared following the sixth injection and swelling of hands and nodes continued to decrease. Following the seventh injection, the patient was asymptomatic and there were no terminal phalangeal swellings or nodes.

EXAMPLE 11

The patient in this example was a male, age 59, with a diagnosis of chronic gouty arthritis, severe, two years duration. Patient had not been able to work at his job for the past year (foreman of large construction firm). Previous therapy included steroids for one year without relief of symptoms. Prior to Acutalyn therapy, both feet were bulging with shoes loosely laced; patient unable to tie shoe laces, etc., because of large nodular deformed fingers and wrists; unable to write name or clench fists; both knee joints badly swollen with much crepitus and joint mica; unable to elevate arms above head due to pain in shoulders; facial expression that of a chronically ill person suffering from severe pain. Laboratory blood chemistries: Serum Uric Acid 6.2 mgm.%; Sedimentation rate 38 mm./hr.

A total of four 5.0 cc. injections of Acutalyn Crude, 50 mg.%; i.v., were given over an 18-day period. Following the first injection, swelling in both feet and pain completely disappeared overnight; the patient's shoes were loose and he could move about with ease, extend his arms over his head, and write with a pen. After each of the next three injections, the patient showed marked improvement. He could move about easily, write, clench his fists, and all nodules were disappearing gradually. Following the last injection, the patient was able to resume his occupation as construction foreman.

EXAMPLE 12

The patient was a female, age 35, with a diagnosis of recurrent, severe, calcific subdeltoid bursitis, 3 years duration, complete disability. Previous therapy included numerous intrabursal injections of hydrocortisone with slight relief followed by aggravation of symptoms; also salicylates, and other conventional therapy. Examination revealed calcific subdeltoid bursitis, left shoulder, with complete restriction of motion of arm; arm in sling; marked tenderness, swelling, tip of left shoulder; patient unable to sleep because of constant pain day and night; patient sick looking and tired. X-ray of left shoulder revealed 1 × 2 cc. diameter calcium deposit in soft tissues adjacent to the superior lateral margin head of humerus. Seven 5.0 ml. injections of Acutalyn crude, 50 mg.%, were given over a period of 10 days. Patient began to respond following the third injection and was able to move arm slightly. Following the fourth injection, the sling was no longer required and the patient was able to sleep. Following the sixth injection, the patient was asymptomatic, with full range of motion in left arm, all angles, and she reported complete relief from pain and a feeling of well-being.

EXAMPLE 13

The following example illustrates the utility of Acutalyn Crude for the treatment of Cirrhosis of the liver. The patient was a 56-year old male, in hepatic coma for four days, with a diagnosis of advanced cirrhosis of the liver, resulting from regular intake of alcohol. Prior therapy initiated upon his entry into the hospital nine days earlier included transfusions, i.v. fluids, multiple vitamins, mucuhydrin, digitalis. Patient's condition continued to deteriorate and three days after hospitalization the patient went into hepatic coma. Arginine i.v. was added to his conventional therapy starting the fifth day, but his condition continued to deteriorate, the coma deepened, spasticity and abnormal neurological changes developed, the patient suffered a cerebral vascular accident, and on the seventh day, the patient was moribund. Upon examination, the patient was unconscious, with severe jaundice, ascites, and edema. The liver was severely enlarged, Babinski positive on right, right arm and leg spastic, and there were additional abnormal neurological changes. Laboratory tests revealed esophageal varices; ECG borderline abnormal; SGOT 74; cephalin flocc. 4+; serum bilirubin direct 5.4, total 9.8; BSP 41%; Hgb 9.9 gr.; WBC normal; anisocytosis; serum protein 5.8. Beginning the ninth day when the patient was moribund, 5.0ml. injections of Acutalyn Crude, 50 mg.%, were given I.M. daily for six days. The patient began to respond after the first injection. Two days later he was awake, cooperative, hallucinating; bilirubin dropped to 2.6 direct, total 4.4; icterus index dropped to 18. The following day the patient was walking. Acutalyn Crude injections, I.M. or I.V., were resumed on the eighth day and given daily or every two days for six weeks. The patient continued to improve, bilirubin dropped to 1.6 direct, total 3.1; thymol turbidity 12, and the patient was released from the hospital. Two years later the patient was hospitalized again with severe prostatic obstruction, rising azotemia, impending clinical uremia, extremely poor renal function, elevated blood ammonia 310 mcg., and hepatic coma. Because of hepatic disease, surgical procedure for the prostatic obstruction was not performed. Arginine i.v. was administered. His condition worsened, and he was threatened with terminal hepatic failure and not expected to live through the night. An injection of Acutalyn Crude, 50 mg.% was given on an emergency basis and the patient again recovered from the hepatic coma. Nine additional injections were given and the patient was discharged from the hospital under the care of his regular physicians.

EXAMPLE 14

The following example illustrates the utility of Acutalyn crude for the treatment of hepatitis in humans. The patient was a male, age 58, with a diagnosis of chronic serum hepatitis. (Patient had trans urethral resection five months earlier and was given two transfusions because of severe hemorrhaging.) All accepted conventional methods of therapy were tried, but the patient continued a downward course. The patient was jaundiced, with bile in urine; the liver was tender and enlarged, three to four finger breadths below right costal margin. Jaundice had been increasing in severity and the patient was weak and tremendously fatigued, very sick, and apprehensive. Cephalin flocc. was 2+. Patient was given 5.0 ml. injections of Acutalyn crude, 50 mg.%, once a week for two weeks, then two injections one month later. At the time of the fourth injection the patient was completely asymptomatic, able to work, and to perform his usual duties. Cephalin flocc. was 1+ and bilirubin reduced to 0.62.

It is therefore apparent that the drug of this invention has great utility for a wide variety of disease conditions. The method of treating these and other conditions with Acutalyn crude accomplishes these purposes. The precise composition of Acutalyn crude is not known, but its biological activity apparently is due in part to the superoxide dismutuse activity of the protein mixture.

We claim:

1. A composition comprising (a) a pharmaceutically compatible excipient, (b) an inflammation inhibiting amount of corticosteroid, and (c) a biologically effective amount for the treatment of disease in mammals of protein mixture for enhancing metabolic functions derived by:

1 treating liver with an aqueous solution of divalent metal activating cation at a pH essentially neutral or slightly alkaline and separating the resultant solids from the liquid;

2. treating the liquid with heavy metal precipitating agent and separating the resultant precipitate from the liquid;
3. adjusting the pH of the liquid from step (2) to a range of between 8.3 and 8.5 and separating the resultant precipitate from the liquid;
4. treating the liquid from step (3) with a concentrated solution of salting out agent to precipitate undesired protein and separating the protein precipitate from the liquid;
5. adding solvent to the liquid from step (4) in an amount sufficient to give the resultant mixture a solvent concentration of 20 to 26% by volume and separating the resultant precipitate from the liquid; adding solvent to the liquid in an amount sufficient to give the resultant mixture a solvent concentration to 35 to 40% by volume to produce a mixture having three layers; separating the upper layer and adding to it in amount sufficient to give the resultant mixture a solvent content 70 and 77% by volume whereby protein is precipitated;
6. separating the protein precipitate and dispersing it in a solvent at a pH of 7.8 to 8.2;
7. dialyzing the dispersion from step (6);
8. heating the dialyzate from step (7) to a temperature between 46 and 50° C. and separating the resultant precipitate from the liquid;
9. subjecting the liquid from step (8) to electrophoresis and recovering a biologically active protein mixture.

2. A method of treating disease conditions in the group consisting of cirrhosis of the liver, scar tissue, tissue damage, wounds and arthritis comprising administering a therapeutically effective amount of protein mixture derived by:
1. treating liver with an aqueous solution of divalent metal activating cation at a pH essentially neutral or slightly alkaline and separating the resultant solids from the liquid;
2. treating the liquid with heavy metal precipitating agent and separating the resultant precipitate from the liquid;
3. adjusting the pH of the liquid from step (2) to a range of between 8.3 and 8.5 and separating the resultant precipitate from the liquid;
4. treating the liquid from step (3) with a concentrated solution of salting out agent to precipitate undesired protein and separating the protein precipitate from the liquid;
5. adding solvent to the liquid from step (4) in an amount sufficient to give the resultant mixture a solvent concentration of 20 to 26% by volume and separating the resultant precipitate from the liquid; adding solvent to the liquid in an amount sufficient to give the resultant mixture a solvent concentration to 35 to 40% by volume to produce a mixture having three layers; separating the upper layer and adding to it in amount sufficient to give the resultant mixture a solvent content 70 and 77% by volume whereby protein is precipitated;
6. separating the protein precipitate and dispersing it in a solvent at a pH of 7.8 to 8.2;
7. dialyzing the dispersion from step (6);
8. heating the dialyzate from step (7) to a temperature between 46° and 50° C. and separating the resultant precipitate from the liquid;
9. subjecting the liquid from step (8) to electrophoresis and recovering a biologically active protein mixture.

3. A method of facilitating tissue repair in mammals comprising administering a therapeutically effective amount of the composition of claim 2.

4. A method of treating cirrhosis of the liver in mammals comprising administering a therapeutically effective amount of the composition of claim 2.

5. A method of treating scar tissue in mammals comprising administering a therapeutically effective amount of the composition of claim 2.

6. A method of treating arthritis in mammals comprising administering a therapeutically effective amount of the composition of claim 2.

7. A method of simultaneously inhibiting inflammation and facilitating wound healing in mammals comprising administering a therapeutically effective amount of the composition of claim 2.

* * * * *

UNITED STATES PATENT AND TRADEMARK OFFICE
CERTIFICATE OF CORRECTION

PATENT NO. : 4,024,247
DATED : 17 May 1977
INVENTOR(S) : Jack G. Fortini et al.

It is certified that error appears in the above-identified patent and that said Letters Patent are hereby corrected as shown below:

Column 6, line 44, delete "the animal" and insert therefor -- animal No. 2 --;

Column 6, lines 57 and 58, delete "one injection of the Acutalyn crude" and insert therefor -- 100 units of Fraction A --.

Signed and Sealed this

Thirty-first Day of January 1978

[SEAL]

Attest:

RUTH C. MASON
Attesting Officer

LUTRELLE F. PARKER
Acting Commissioner of Patents and Trademark